(12) United States Patent
Kammer et al.

(10) Patent No.: US 7,560,667 B2
(45) Date of Patent: Jul. 14, 2009

(54) HEATING ELEMENT FOR LIQUID WARMING DEVICE

(75) Inventors: Patrick Kammer, Greensboro, NC (US); Kevin Joseph Rackers, Summerfield, NC (US)

(73) Assignee: C Change Surgical LLC, Winston-Salem, NC (US)

( * ) Notice: Subject to any disclaimer, the term of this patent is extended or adjusted under 35 U.S.C. 154(b) by 0 days.

(21) Appl. No.: 11/209,430

(22) Filed: Aug. 23, 2005

(65) Prior Publication Data

US 2006/0086361 A1  Apr. 27, 2006

Related U.S. Application Data

(60) Provisional application No. 60/603,956, filed on Aug. 24, 2004, provisional application No. 60/603,957, filed on Aug. 24, 2004.

(51) Int. Cl.
*A61B 19/00* (2006.01)
*A61F 7/00* (2006.01)
*F27D 11/00* (2006.01)
*H05B 3/36* (2006.01)

(52) U.S. Cl. .................. 219/432; 219/430; 219/433; 219/439; 219/528; 219/549; 600/114

(58) Field of Classification Search .................. None
See application file for complete search history.

(56) References Cited

U.S. PATENT DOCUMENTS

| | | | | |
|---|---|---|---|---|
| 2,018,512 A * | 10/1935 | De Laney et al. | ............ | 219/528 |
| 2,682,602 A * | 6/1954 | Huck | .......................... | 219/433 |
| 2,844,696 A * | 7/1958 | Custer, Jr. | .................. | 219/213 |
| 2,892,066 A * | 6/1959 | Springer | .................... | 219/435 |
| 3,031,565 A | 4/1962 | Appleton et al. | .............. | 219/44 |
| 3,231,718 A * | 1/1966 | Vasile | .................... | 219/450.1 |
| 3,513,297 A * | 5/1970 | Jordan | ........................ | 219/545 |
| 3,751,629 A * | 8/1973 | Eisler | .......................... | 219/201 |
| 3,767,898 A | 10/1973 | Wells et al. | .................. | 219/441 |
| 3,974,358 A * | 8/1976 | Goltsos | ....................... | 219/387 |
| 4,419,568 A | 12/1983 | Van Overloop | ............. | 219/441 |
| 4,700,050 A | 10/1987 | Hennuy et al. | .............. | 219/438 |
| 4,934,152 A | 6/1990 | Templeton | ..................... | 62/66 |
| 4,967,057 A * | 10/1990 | Bayless et al. | .............. | 219/549 |
| 4,967,061 A | 10/1990 | Weber, Jr. et al. | ........... | 219/438 |
| 5,129,033 A | 7/1992 | Ferrara et al. | ................ | 392/447 |

(Continued)

OTHER PUBLICATIONS

American Society of PeriAnesthesia Nurses, "Clinical Guideline For The Prevention Of Unplanned Perioperative Hypothermia", 15 printed pages, published approx. Oct. 2002. www.aspan.org.

(Continued)

*Primary Examiner*—Joseph M Pelham
(74) *Attorney, Agent, or Firm*—The Eclipse Group LLP; Kevin E. Flynn

(57) ABSTRACT

This disclosure provides examples of innovations for a heating pad to be used with heating removable basins or drapes containing sterile fluid. When used with a sterile basin, it is desirable for the pad to deform to conform to the irregular surface on the bottom of the basin. It is also desirable for the pad to have a low thermal mass so that the pad is more responsive to the control system.

7 Claims, 13 Drawing Sheets

U.S. PATENT DOCUMENTS

| | | | | |
|---|---|---|---|---|
| 5,174,306 | A | 12/1992 | Marshall | 128/849 |
| 5,271,085 | A | 12/1993 | Carballo | 392/444 |
| 5,435,322 | A * | 7/1995 | Marshall | 128/849 |
| 5,451,747 | A * | 9/1995 | Sullivan et al. | 219/528 |
| 5,551,240 | A | 9/1996 | Faries, Jr. et al. | 62/3.6 |
| 5,591,365 | A * | 1/1997 | Shields | 219/213 |
| 5,614,292 | A * | 3/1997 | Saylor | 428/209 |
| 5,615,423 | A | 4/1997 | Faries, Jr. et al. | 4/639 |
| 5,653,938 | A | 8/1997 | Faries, Jr. et al. | 422/3 |
| 5,729,653 | A | 3/1998 | Magliochetti et al. | 392/485 |
| 5,879,621 | A | 3/1999 | Faries, Jr. et al. | 422/3 |
| 6,087,636 | A * | 7/2000 | Faries et al. | 219/429 |
| 6,091,058 | A | 7/2000 | Faries, Jr. et al. | 219/430 |
| 6,184,496 | B1 * | 2/2001 | Pearce | 219/213 |
| 6,211,493 | B1 * | 4/2001 | Bouman | 219/213 |
| 6,255,627 | B1 | 7/2001 | Faries, Jr. et al. | 219/430 |
| 6,259,067 | B1 | 7/2001 | Faries, Jr. et al. | 219/428 |
| 6,294,762 | B1 | 9/2001 | Faries, Jr. et al. | 219/400 |
| 6,371,121 | B1 | 4/2002 | Faries, Jr. et al. | 128/849 |
| 6,372,323 | B1 * | 4/2002 | Kobe et al. | 428/119 |
| 6,384,380 | B1 | 5/2002 | Faries, Jr. et al. | 219/385 |
| 6,392,206 | B1 * | 5/2002 | Von Arx et al. | 219/468.1 |
| 6,433,317 | B1 * | 8/2002 | Arx et al. | 219/468.1 |
| 6,768,085 | B2 | 7/2004 | Faries, Jr. et al. | 219/494 |
| 6,860,271 | B2 | 3/2005 | Faries, Jr. et al. | 128/849 |
| 6,884,970 | B2 * | 4/2005 | Lehman | 219/432 |
| 6,910,485 | B2 | 6/2005 | Faries, Jr. et al. | 128/849 |
| 6,918,395 | B2 | 7/2005 | Faries, Jr. et al. | 128/849 |
| 7,038,177 | B2 * | 5/2006 | Rock | 219/529 |
| 7,176,030 | B2 | 2/2007 | Faries, Jr. et al. | 436/1 |
| 7,268,320 | B2 * | 9/2007 | Rock et al. | 219/211 |
| 2002/0043260 | A1 | 4/2002 | Layer et al. | 126/263.01 |
| 2004/0065314 | A1 | 4/2004 | Layer et al. | 126/263.03 |
| 2005/0242086 | A1 | 11/2005 | Imura | 219/627 |
| 2006/0011608 | A1 | 1/2006 | Lehman | 219/432 |

OTHER PUBLICATIONS

Sessler et al., "Nonpharmacological Prevention of Surgical Wound Infections", *Clinical Infectious Diseases*, CID 2002:35 (Dec. 1) pp. 1397-1404. Published electronically Nov. 13, 2002 by Infectious Diseases Society of America.

"Clinical Guideline For The Prevention Of Unplanned Perioperative Hypothermia", *American Society of PeriAnesthesia Nurses*, published approx. Oct. 2002. www.aspan.org.

Sessler et al., "Nonpharmacological Prevention of Surgical Wound Infections", *Clinical Infectious Diseases*, CID 2002:35 (Dec. 1) pp. 1397-1404. Published electronically Nov. 13, 2002 by Infectious Diseases Society of America.

Statement of Reasons for Allowance for related U.S. Appl. No. 11/209,283, 2 pgs. (Aug. 7, 2006).

* cited by examiner

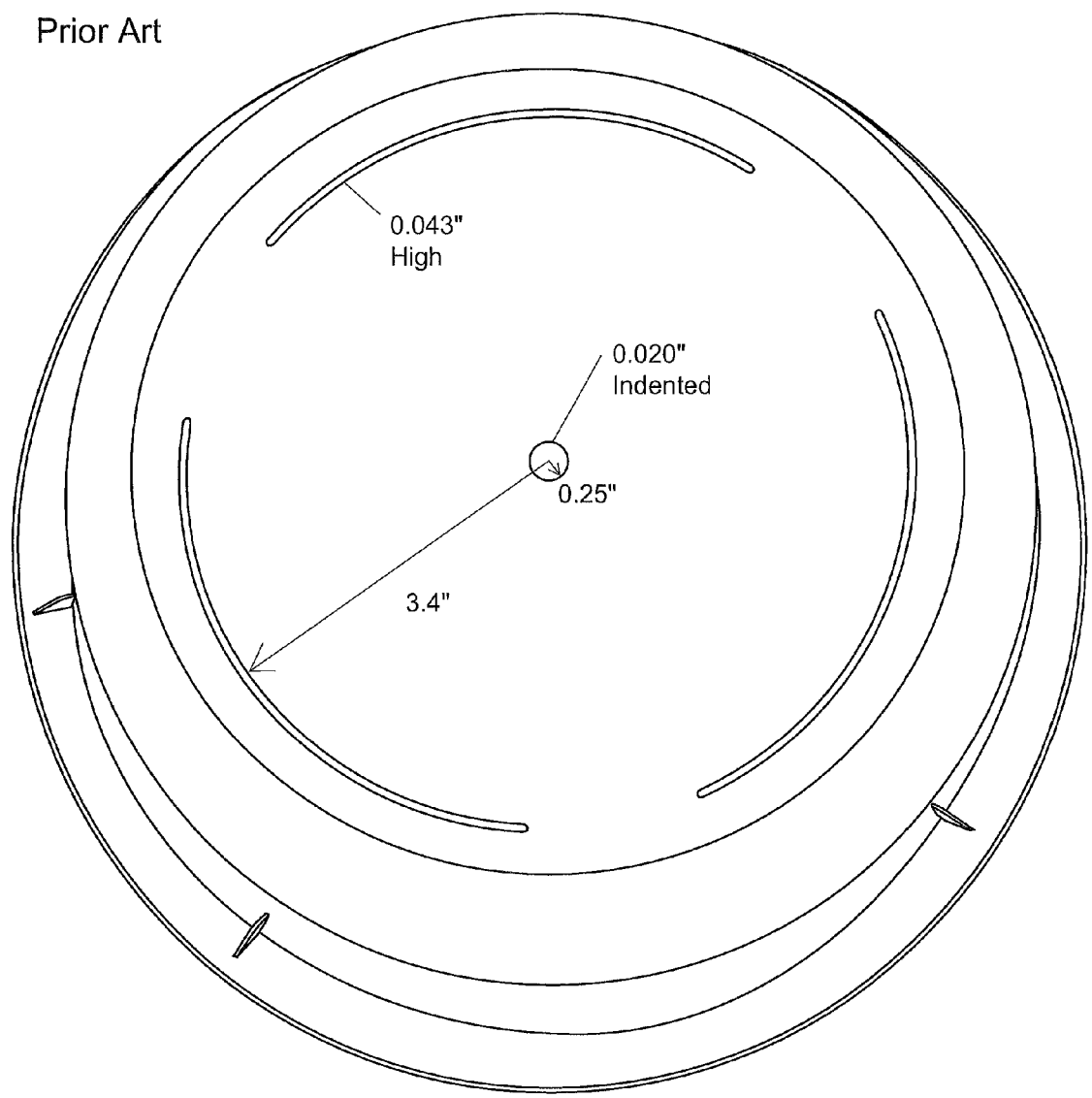

HEATING ELEMENT FOR LIQUID WARMING DEVICE

This application claims priority to and incorporates by reference herein, two provisional patent applications: U.S. Provisional Patent Application 60/603,957 for Heating Element for Liquid Warming Device filed Aug. 24, 2004 and U.S. Provisional Patent Application 60/603,956 for Liquid Warming Device and Control System filed Aug. 24, 2004.

FIELD OF THE INVENTION

This invention relates to improvements in methods and apparatus for heating of sterile surgical liquids. More specifically, this invention relates to a particular type of heating element for the heating of the sterile surgical liquids. Even more specifically, the invention relates to a warming pad adapted to provide heat to in order to provide a controlled amount of heat indirectly to sterile surgical liquids.

RELATED APPLICATIONS

Assignee has filed a co-pending U.S. patent application Ser. No. 11/209,283 for Liquid Warming Device With Basin that could benefit from aspects of the improved heating element described in the present application. As the improved heating element of the present application could be applied beneficially to a wide variety of liquid warming devices or for devices for providing surgical slush, present description will not duplicate the material found in the Liquid Warming Device and Basin application, but that material is incorporated herein by reference with the understanding that the incorporated material does not impose any restrictions on the scope of the present invention.

BACKGROUND OF THE INVENTION

Devices for the heating of sterile surgical liquids are known in the art. In a wide variety of surgical procedures, sterile fluids are used to irrigate the site of the surgery. It is important that the temperature of the fluids used be strictly controlled. As the portion of the brain that regulates body temperature is shut down with anesthesia, it is important that the introduction of sterile fluids does not cool the body core temperature. Clinical studies have indicated that a range of adverse consequences arise from a change in body core temperature of as few as one to three degrees Celsius. The adverse consequences from mild perioperative hypothermia include hypertension and increased vascular resistance, cardiac events, coagulopathy, an increase risk of surgical wound infections, and delays in the body's ability to remove drugs from its systems. Another specific adverse consequence is shivering which can increase metabolic rate up to 500% and thus increase demands for oxygen and the need to clear carbon dioxide. This list of complications is by no means exhaustive, but it illustrates the critical importance in controlling the body core temperature. Careful control of the temperature of sterile irrigation fluids is an important part of controlling body core temperature.

The prior art includes various devices for warming sterile fluid. Some are incorporated into a rolling cabinet for placement in a convenient place within the sterile field in an operating room so that sterile fluid is available at an appropriate temperature for use in the surgery such as irrigation or lavage.

One prior art solution is depicted in FIG. 1. Before describing the contents of FIG. 1 it is appropriate to note that FIG. 1 and the other figures that follow are adapted to facilitate a presentation of the teachings of the present invention. As such, the Figures are not intended to convey the precise relative dimensions of the various components. For example, surgical drapes are referenced in a number of figures and these drapes have been drawn with relatively thicknesses that are out of proportion so that the drape layer can be readily seen in the diagram.

Returning to FIG. 1, a cabinet 104 with an integrated and permanently attached metal basin ("integrated basin") 108 provides a cavity for receipt of sterile fluids. In order to provide a separation between the sterile field and the reusable cabinet with integrated basin, a custom fit surgical drape 112 is laid on the cabinet and matches the cavity formed by the integrated basin. The sterile fluid 116 is placed in the drape.

A conventional heater 118 comprised of etched foil strips 120 in a slab 124 of silicon rubber is connected by an adhesive (not shown) to the underside of the integrated basin 108. A temperature measuring device 128 provides an input to controller 132 which turns on and off the power provided to heater 118. The controller 132 receives instructions from a user to increase or decrease the set point temperature for the heater 118 based on the user's desire to increase or decrease the temperature of the surgical fluid 116.

It is recognized as desirable that the heating process of the basin containing the fluids be capable of quickly heating fluid to bring it to the appropriate temperature. It is also recognized that having localized hot spots is undesirable as is using a heater that can apply so much heat that it can damage the surgical drape. Use of a heater that can expose personnel to heated surfaces that are hot enough to cause injury is undesirable and in some cases contrary to governmental regulations.

The integrity of the sterile field is important during surgery. Any breach that might indicate that the sterile field has become contaminated is taken very seriously. A breach that is undiscovered for a period of time is especially troublesome as it is difficult to assess when the breach was created and whether it caused the patient to be exposed to contaminants while vulnerable during surgery. Thus, it is no wonder that concerns from breaches in the sterile drapes 112 were taken very seriously. U.S. Pat. No. 6,910,485 for Medical Solution Thermal Treatment System and Method of Controlling System Operation in Accordance with Detection of Solution and Leaks in Surgical Drape Container addresses this concern Likewise, issued U.S. Pat. No. 6,091,058 for Thermal Treatment System and Method for Maintaining Integrity and Ensuring Sterility of Surgical Drapes Used with Surgical Equipment teaches ways of reducing the risk of damage to surgical drapes from objects placed in the drape covered basin.

Thus, problems associated with the recognized risk of a breach in a sterile drape have led others to develop various ways of reducing this risk or at least quickly detecting the breach.

In order to provide peace of mind to those working in the surgical theater, it would be advantageous to provide a way to use a disposable basin or a freestanding metal basin that could be sterilized.

Plastic basins are ubiquitous in hospitals and are used in many ways. Plastic basins that are sterilized (for example through irradiation or ethylene oxide gas sterilization) can safely be used in the sterile field without a surgical drape. In fact it is already extremely common to use a sterilized plastic basin in the sterile field to hold sterile fluids, so surgical room staff are confident that a plastic basin is sufficiently durable to handle the full range of abuse that can come from such use. Although recognized as durable, these simple unheated plastic basins cannot hold the sterile fluids above ambient temperature for an indefinite period of time.

An alternative to plastic basins is metal basins that are sterilized and safely reused just as a range of surgical implements are sterilized and reused.

The use of such basins would provide peace of mind as it is difficult to conceive of any activity in the sterile field that could cause a breach in a non-defective plastic or metal basin. A secondary benefit would be that standard gradation marks on the inside walls of the removable basin would provide a visual indication of the amount of sterile fluid remaining in the removable basin. As using basin gradation marks is done by hospital personnel in other contexts including short term holding of pre-heated sterile fluid in operating rooms, the use of fluid gradation marks in this context will seem familiar.

Using removable basin inside the sterile drape found in FIG. 1 is not without problems. Turning now to FIG. 2, a sterile removable basin 204 such as a sterile plastic basin has been placed on top of existing surgical drape 112. This provides the peace of mind from having a substantial removable basin 204 to contain the sterile fluid 116 without fears for the integrity of the surgical drape 112. The surgical drape 112 still has a role in isolating the liquid warming device cabinet 104 and the integrated basin 108 from the sterile field.

As in FIG. 1, a conventional heater 118 comprised of etched foil strips 120 in a slab 124 of silicon rubber is connected by an adhesive (not shown) to the underside of the integrated basin 108. A temperature measuring device 128 provides an input to controller 132 which turns on and off the power provided to heater 118. The controller 132 receives instructions from a user to increase or decrease the set point temperature for the heater 118 based on the user's desire to increase or decrease the temperature of the surgical fluid 116.

In order to examine the problems that would arise from the simple addition of a removable basin 204, it is necessary to examine what happens when it comes time to increase the temperature of sterile fluid 116. When the set point used by controller 132 exceeds the temperature measured at temperature measuring device 128 the heater 118 is turned on. As the slab 124 of silicon rubber has a non-zero specific heat, some of the heat from the heater goes to heat the slab 124 so the heated slab 124 can in turn increase the temperature of the bottom of the integrated basin 108 in the top of the liquid warmer device cabinet 104. The integrated basin 108 has its own non-zero specific heat and thus its own thermal mass which must be moved to a new higher temperature.

As the integrated basin 108 heats up, it passes some heat through the surgical drape 112 to the bottom of the removable basin 204. Unfortunately, the top of the integrated basin 108 and the bottom of the removable basin 204 do not mate perfectly so there are points of contact 136 with surgical drape 112 sandwiched between but also regions of air 140 which serve as insulators to slow the passage of heat from the top of the integrated basin 108 and the bottom of the removable basin 204. The air pockets 140 can be above or below the surgical drape 112. Points of contact work well for transferring heat; conversely, the presence of these air regions slows the transfer of heat and causes some spots on the removable basin 204 to be hotter than other spots.

The adjustment of the prior art solution as shown in FIG. 1 to use a substantial removable basin 204 is not optimal with respect to efficiently imparting heat to a basin and avoiding the creation of hot spots on the bottom of the basin. The magnitude of the problem is driven largely by the degree to which the bottoms of the removable basins are not flat or otherwise uniform. To a lesser extent, the problem is exacerbated by irregularities in the upper surface of the integrated basins 108.

An additional problem with this modification to the prior art is an aggregated thermal mass that is relatively high and there are a number of insulators, thus slowing any change in the temperature of the surface contacting the removable basin, drape, or other container. The thermal mass problem slows the response of the system both to increase heat and to decrease the heat.

FIGS. 3(A)-(C) shows the bottoms of three different removable basins that could be used as removable basin 204 in FIG. 2. The basins include protrusions outward (downward when the removable basin is positioned so that it can receive fluid) and indentations into the surface of the removable basin. Each basin bottom poses its own problems. The basin shown in FIG. 3(A) has three arc-shaped ridges that rise 0.054 inches outward. There are also two circular ridges with one located away from the center of the basin bottom.

FIG. 3(B) has a combination of another set of arc-shaped ridges but a different height and different radial distance from the center than those found in FIG. 3(A). A second complication is an indented region at the center of the basin bottom.

FIG. 3(C) poses yet another problem as the empty basin starts out with effectively only an outer ring that makes contact as there is a indentation of 0.025 inches for the majority of the bottom surface and an extra indentation of another 0.025 inches in a region at the center of the basin bottom.

There three examples are not exhaustive of all the irregularities found in removable basin bottoms, but they do illustrate the magnitudes and types of irregularities. One can appreciate that it would be difficult to design a corresponding set of irregularities into the surface of the integrated basin in order to promote surface to surface contact between basins (ignoring the surgical drape for a moment). Even if one could implement the appropriate set of reversed indentations and protrusions, the irregular symmetry around the center of the basin bottom would require alignment guides to help line up the various arcs or non-centered rings on the removable basin bottom with the corresponding portions of the integrated basin. The problem is greatly magnified if the goal is to be able to provide good surface to surface contact between the integrated basin and several different removable basin bottoms.

SUMMARY OF THE DISCLOSURE

This disclosure provides examples of innovations for a heating pad to be used with heating removable basins or drapes containing sterile fluid. When used with a sterile basin, it is desirable for the pad to deform to conform to the irregular surface on the bottom of the basin. It is also desirable for the pad to have a low thermal mass so that the pad is more responsive to the control system.

DESCRIPTION

The present invention will now be described more fully hereinafter with reference to the accompanying drawings, in order to disclose selected embodiments. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
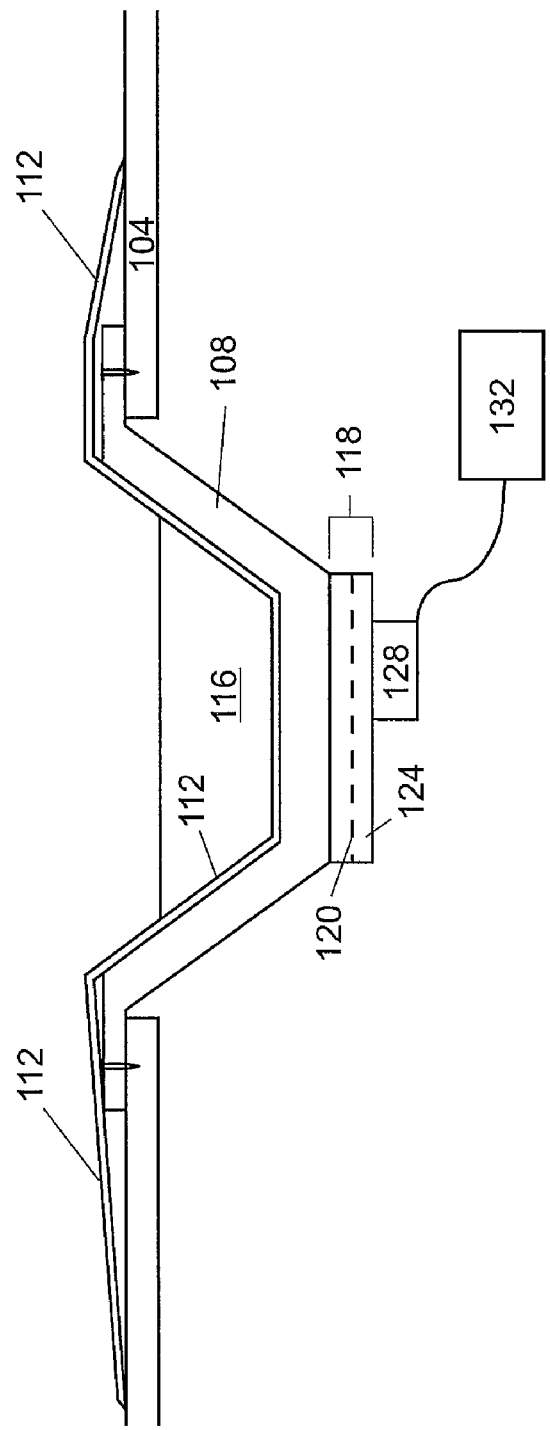
FIG. 1 shows a prior art solution of placing fluid 116 in a sterile drape 112 in a permanent basin in a liquid warming device.
Figure 2:
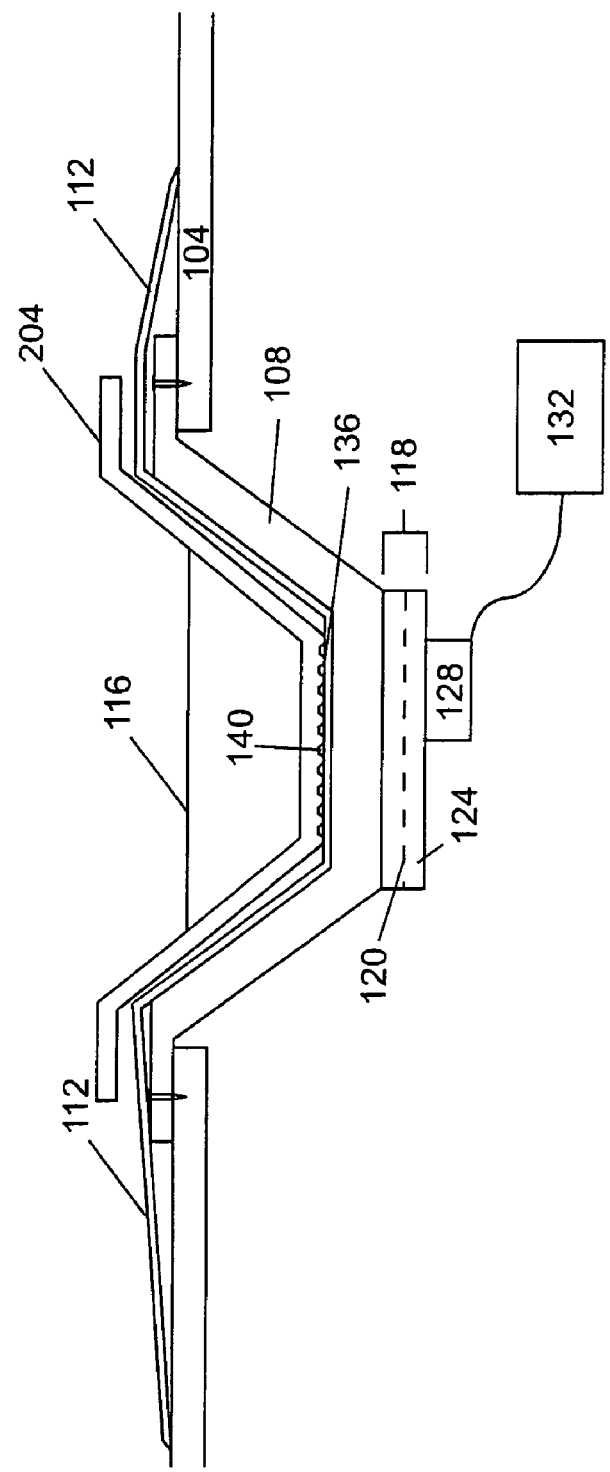
FIG. 2 shows an attempt to overcome the shortcomings of the prior art solution described in connection with FIG. 1 by adding a removable basin 204 above the sterile drape 112.
Figure 3A:
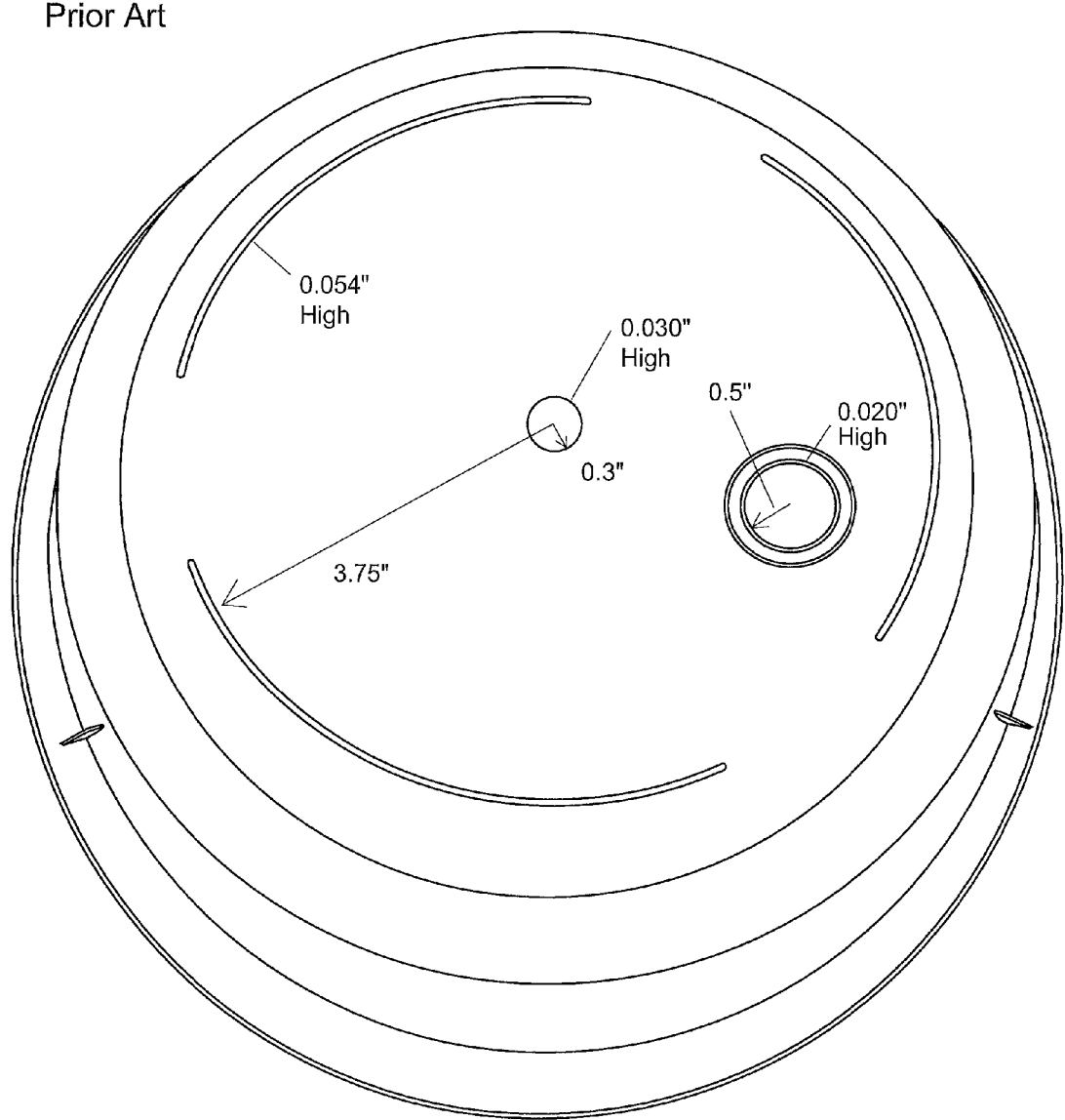
FIG. 3 shows three different basin bottoms to highlight the irregularities in the bottom surfaces.
Figure 3C:
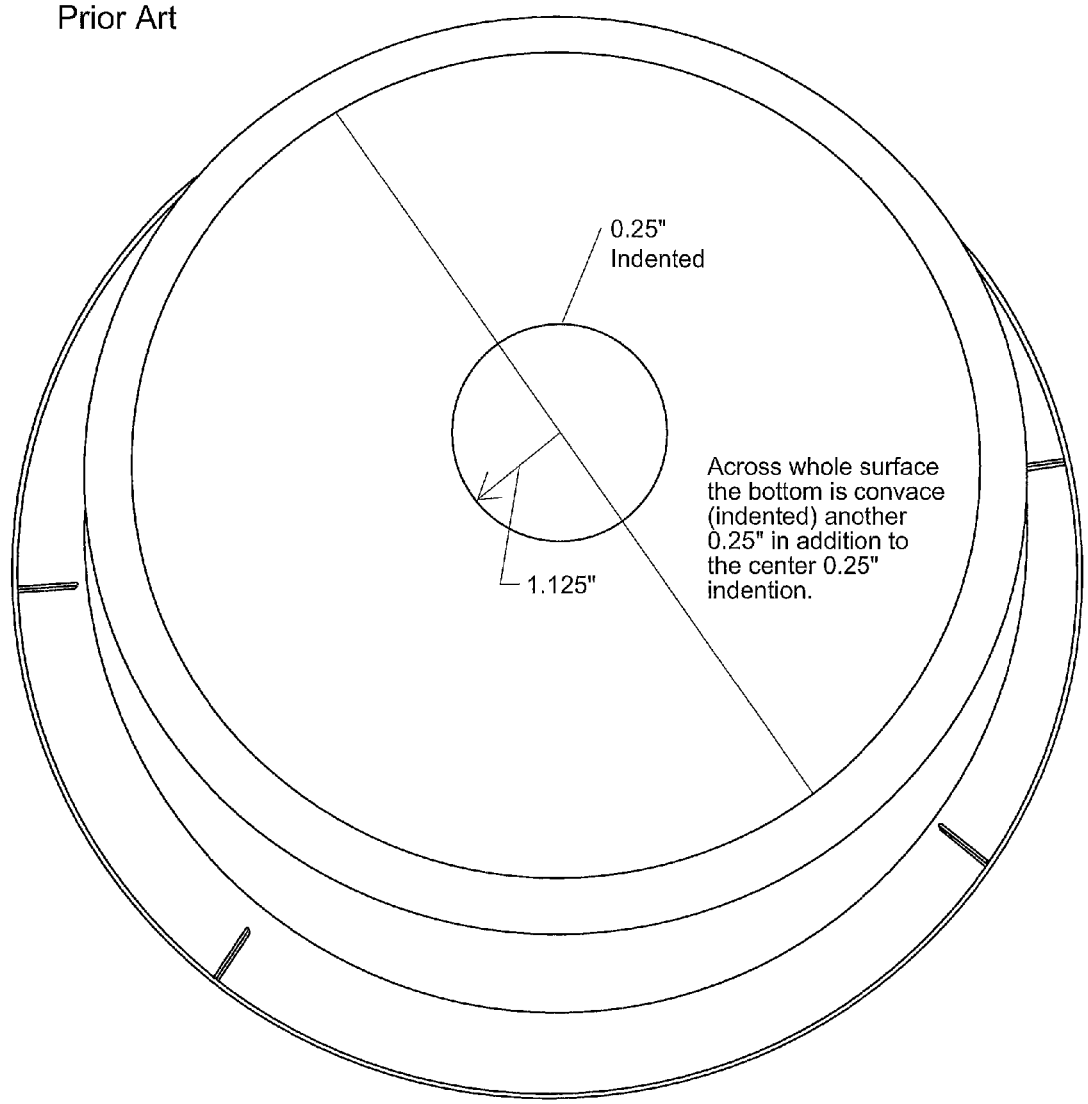
Figure 4:
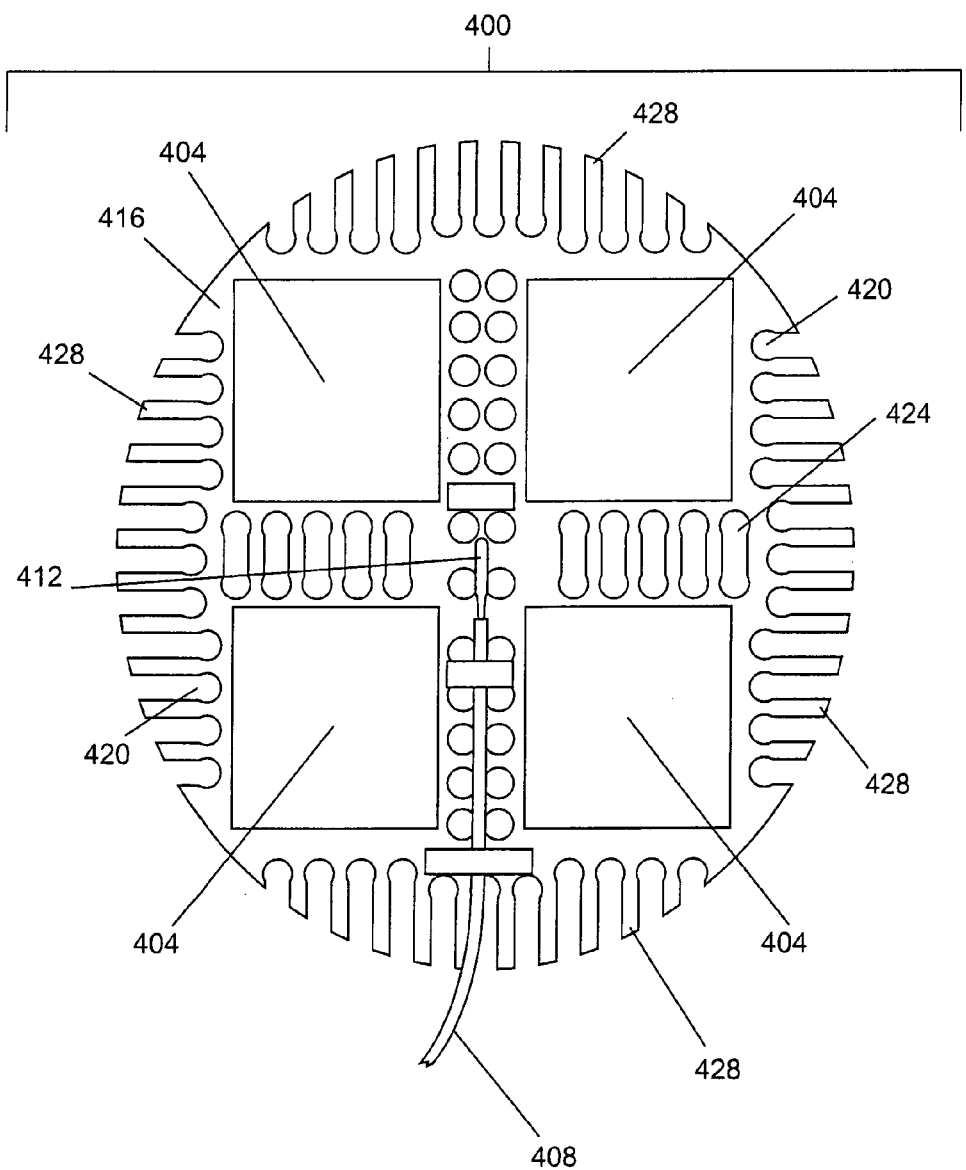
FIG. 4 illustrates one exemplary embodiment of a heating unit layer of a warming pad.
Figure 5:
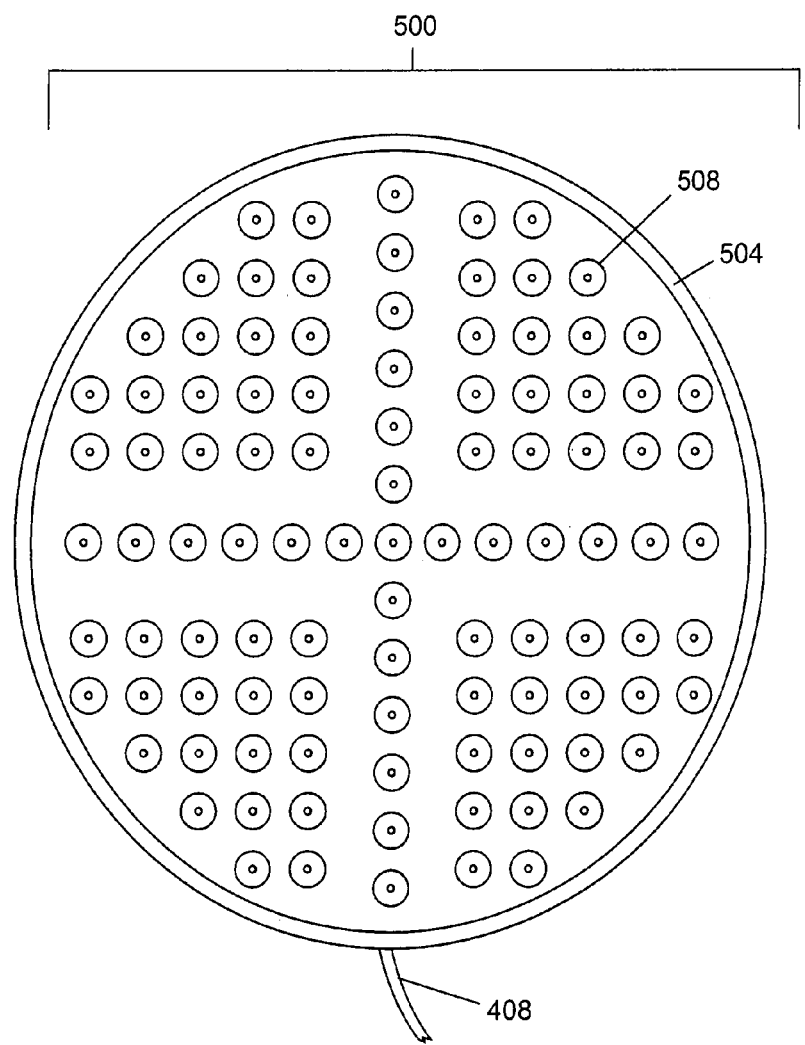
FIG. 5 illustrates one example of a bottom surface of a warming pad made in accordance with the present invention.

FIG. 4 illustrates one exemplary embodiment of a heating unit layer 400 of a warming pad of the present invention. In order to show the relationship of the heaters to the other components, FIG. 4 shows the bottom side of the heating unit layer 400. FIG. 5 illustrates one example of a bottom surface of a warming pad 500 made in accordance with the present invention. The top surface of the warming pad would be smooth in a preferred embodiment and is thus not shown.

Returning to FIG. 4, a set of four off-the-shelf 45 watt heaters 404 are arranged in a grid pattern and provided power through wires 408 which are in turn controlled by whatever control system (not shown) is used with this fluid warming device. The present invention is not limited to four heaters arranged 2 by 2 as the present invention does not selectively operate individual heaters. To the contrary any number of heaters can be used as long as the overall pattern is sufficiently large to serve the purpose of delivering heat to the approximate area in contact with the removable basin to be warmed. Applicants believe that one heater may ultimately be the preferred embodiment. A custom patterned heater formed by an etching process well known to those of skill in the art is one solution.

A heat sensor 412 is positioned in the center of the heating unit to measure the temperature of the heating unit. An RTD heat sensor is suitable for this task, but the invention is not limited to the use of an RTD heat sensor as those of skill in the art will recognize that other heat sensors could be used. Placing the heat sensor near the center of the grid of heating units provides a more accurate indication of average heating unit temperature. The placement of the heat sensor would not necessarily be in the center if a single heat unit is used. Some heaters come with a mechanical thermostat to use as a control device to limit the temperature of the heater in the event that the primary control system fails. The mechanical thermostat opens and thus cuts off power from reaching the heaters if the temperature exceeds a limit that is above the normal operating range for the heater.

As shown in FIG. 4, below the heaters 404 lies a heat distribution layer 416. As FIG. 4 shows the components from below, in actual operation, the heat distribution layer 416 is above the heaters 404 and below the top surface of the heating pad 500. The heat distribution layer 416 is used to distribute heat, including distributing heat from areas under heaters 404 out to the perimeter of the heating unit layer 400. The heat distribution layer 416 will also reallocate heat from areas of the removable basin bottom with a low draw rate for heat to areas having a high draw rate. For example if an empty removable basin was loaded with a cold wet sponge and a kidney-shaped basin partially filled with a warm fluid, then the cold wet sponge would tend to draw heat and cause the control system to provide power to the heater array. The heat distribution layer 416 helps move heat from under the kidney-shaped basin towards the cold sponge.

As it can be desirable to allow the warming pad 500 to flex to adjust to the surface of the bottom of the cavity to receive the removable basin, the heat distribution layer in a preferred embodiment uses perimeter finger gaps 420 and inter-heater zone web gaps 424. As the name implies, the perimeter finger gaps 420 are places where the material in the heat distribution layer 416 was either removed or not created so that the absence of material defines a set of perimeter fingers 428. These perimeter fingers 428 are a compromise between optimizing heat transfer and optimizing flexibility near the perimeter of the warming pad 500 as the minimal interference with flexibility would be the absence of heat distribution layer.

Optionally, the heat distribution layer 416 may also include inter-heater web gaps 424 to increase the flexibility of the heat distribution layer 416. The wires 408 are shown in FIG. 4 running over some of the web gaps 424 but these gaps when seen without the wires present are like the other unobstructed web gaps shown in FIG. 4. It is considered desirable to place the web gaps so that they pose minimal or at least reduced interference to the passage of heat between the regions below adjacent heaters. For example if the web gaps shown in FIG. 4 were replaced with a few long web gaps oriented to be approximately parallel to the long axis of the gap between adjacent heaters, these gaps would interfere with the movement of heat from the zone under one heater to the zone of an adjacent heater that was not providing as much heat as the first heater. Likewise, an area between heaters and partially isolated from the heaters by web gaps would tend to lag behind the temperature of the heaters, especially when the heaters are moving to a new higher temperature.

If the arrangement of heaters is something other than a 2 by 2 grid then the gaps between the heaters would be located at different places than shown in FIG. 4. For example a grid of 3 by 3 heaters would have four lines of inter-heater gaps instead of two intersecting lines shown in FIG. 4.

If a heater is used that incorporate regions within the heater without heater lines, then web gaps could be added to these zones within one heater. Thus, it is not necessary that web gaps be placed between heaters.

The end points of the web gaps and the perimeter finger gaps are curved in the prototype shown in FIG. 4 as this shape is less likely to tear than a square corner. However, one can appreciate that choices of material and other choices can increase the warming pad's resistance to tearing so that curved endpoints are less important and potentially unnecessary.

As a low thermal mass is useful when trying to quickly heat the warming pad and avoid prolonged periods above the target temperature after an overshoot, a preferred material for the heating unit layer is copper foil that is only 2.8 mils thick. This represents a compromise between the desire for a layer to quickly dissipate and equalize heat inside the warming pad and the desire to have a low thermal mass. Those of skill in the art will recognize that other conductive materials could be used in place of copper. A number of different metals have suitable qualities, although copper is a good combination of price and performance. Conductive materials could include materials beyond solids to include any type of material including but not limited to liquids, gels, foams, colloids, ceramics, composites, meshes, fabrics, and gases. Conductive materials could be used in thicknesses other than 2.8 mils thick. This particular teaching can be summarized as thermally conductive material with low thermal mass. The desire for a low thermal mass leads away from the use of a fluid filled pillow (like a water-bed) as such a system would have a high thermal mass. A secondary factor is that the choice of material should be suitable to be flexed repeatedly without breaking and should not unduly stiffen the warming pad as it is desirable for the pad to flex to conform to the irregular shape of the removable basin bottom.

The one or more heaters can be bonded to the heat distribution layer to provide an effective thermal contact between the heater and the heat distribution layer.

Returning to FIG. 5, the bottom face of the warming pad 500 is shown. The bottom face includes an outer rim 504 and a series of protrusions 508. A partial cross section of warming pad 500 is shown in FIG. 6.

Figure 6:
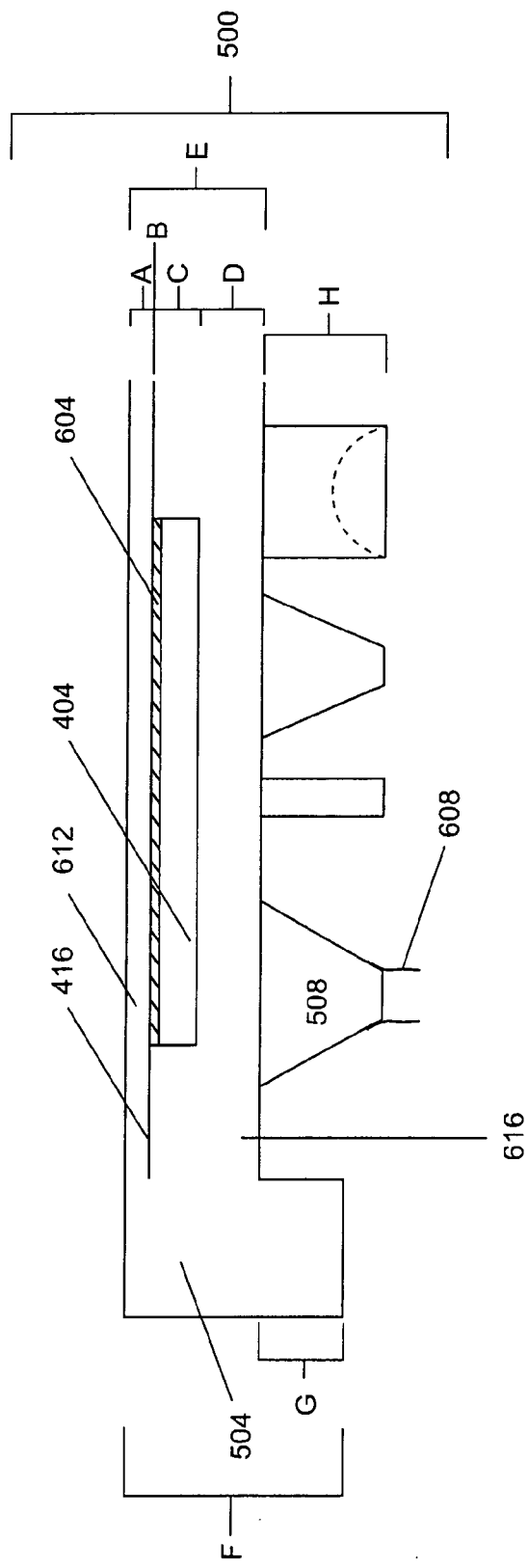
FIG. 6 illustrates a small sample of other possible protrusion shapes.

FIG. 6 shows the outer rim 504 which provides protection against tearing of the warming pad. Note that in the preferred embodiments the protrusions 508 extend downward beyond the outer rim 504 so the readily deformed protrusion tops make contact with the surface below the warming pad. The protrusions of the prototype are conical frustums (cones without the tips). An artifact of the creation of the prototypes is cylindrical flashing 608 from the interaction of an entrapped bubble in the mold. This is suitable but the flashing is not required on protrusions created in accordance with the teachings of this present invention.

FIG. 6 illustrates a small sample of other possible protrusion shapes. The possible shapes include but are not limited to cylinders that are thin enough to easily deform, pyramidal frustums, and shapes such as cylinders with interior voids. The list of potentially useable shapes is more expansive than the few illustrated in FIG. 6. For example hemispheres made of appropriate material could provide the desired characteristics as could non-truncated cones or pyramids. The desirable characteristics of a protrusion include: 1) easy to form, 2) deforms easily to facilitate the movement of the warming pad to conform to the shape of the removable basin bottom, 3) durable so that the protrusions do not break with repeated use and sterilization, 4) suitable for cleaning (does not tend to trap material that is not easily removed during cleaning) and 5) having low thermal conductivity as it is not desirable to draw heat into the protrusions and away from the heaters and the heat distribution layer.

FIG. 6 also shows a heater 404 connected to the heat distribution layer 416 by bonding material 604. Note that in a preferred embodiment, the heat distribution layer 416 approaches the outer rim but does not extend into the outer rim. As illustrated in FIG. 6, the heat distribution layer 416 is much closer to the top of the warming pad than to the bottom of the warming pad. FIG. 6 is useful for conveying concepts relevant to the present invention but FIG. 6 is merely illustrative and not intended to be to scale.

The relative sizes in at least one example of the present invention, are as follows. The material 612 above the heat distribution layer is approximately 0.020 to 0.040 inches (dimension A). In contrast the material 616 below the heater (dimension D) is approximately 0.125 inches. The heaters are approximately 0.012 inches thick (dimension C) while the heat distribution layer 416 is only 0.003 inches thick (dimension B). The thickness at the outer ring is approximately 0.400 inches (dimension F) which is divided into the protruding ring of 0.230 inches (dimension G) and dimension E of 0.170 inches. Note that the height of the protrusions (dimension H) is approximately 0.300 inches which exceeds dimension G.

In a preferred embodiment, the outer rim 504, the protrusions 508, the material 612 above the heat distribution layer, and the material 616 below the heat distribution material are all formed of the same material so that after assembly of the various layers a subsequent processing step can be used to fuse the various layers together. Note that one of the advantages of the use of the perimeter finger gaps 420 and the web gaps 424 is that material from above and below the heat distribution material 416 can fuse together and thus provide additional resistance to internal delamination of the warming pad 500. Likewise fusing a top portion above the outer rim to a bottom portion of the outer rim provides additional resistance against delamination.

Alternatives to fusing the layers together include molding the unit; bonding various layers together; or a combination. These alternatives would not require that the compliant layers above and below the heater/heat distribution layer be made of the same material. Different materials or different variations of silicon could be used for the layers. A suitable processing sequence for a certain level of production volume would be to bond the heaters to the heat distribution layer and then bond a thin layer of silicon (in the range of 0.020 inches) to the heat distribution layer before placing this multilayer unit over a partially set mold of containing the protrusions and the below heater layer of material.

Another alternative would be to bond or otherwise join a thin fluid filled pad (not shown) to the top of the heat distribution layer 416. This thin fluid filled pad would provide the advantage of being very adaptable to the shape of the bottom of the removable basin ("compliant") so as to provide a high degree of contact either directly or indirectly through a sterile drape. However, by being a thin fluid filled pad, the pad would not have the undesired quality of a high thermal mass.

Alternatively, the warming pad could be created by pouring material in the mold to partially fill the mold, adding the heat distribution material with the previously attached heaters, wires, and heat detection device, and then pouring additional material to fill the mold. While this method is suitable for making prototypes and small production runs, it may not be the best way of mass producing warming pads.

A suitable material is a silicon rubber material available from a number of sources as silicon rubber tolerates heat up to temperatures beyond the intended operating range for the warming pad. A mixture of 1 part catalyst to somewhat less than 8 parts silicon compound provided a satisfactory result in the prototype.

Other materials could be used in place of silicon. The characteristics of a desirable material include pliable, tolerant of prolonged exposure to heat (heat tolerant rated for 450 degrees Fahrenheit is sufficient for some applications), and an insulator. As there is only a thin layer of material 612 above the heat distribution layer 416, the insulation effect is not large. In contrast, the relatively thick layer of material 616 below the heat distribution layer 416 and heater(s) 404 serves to thermally insulate and reduce the heat loss through the bottom of the warming pad 500.

Figure 7:
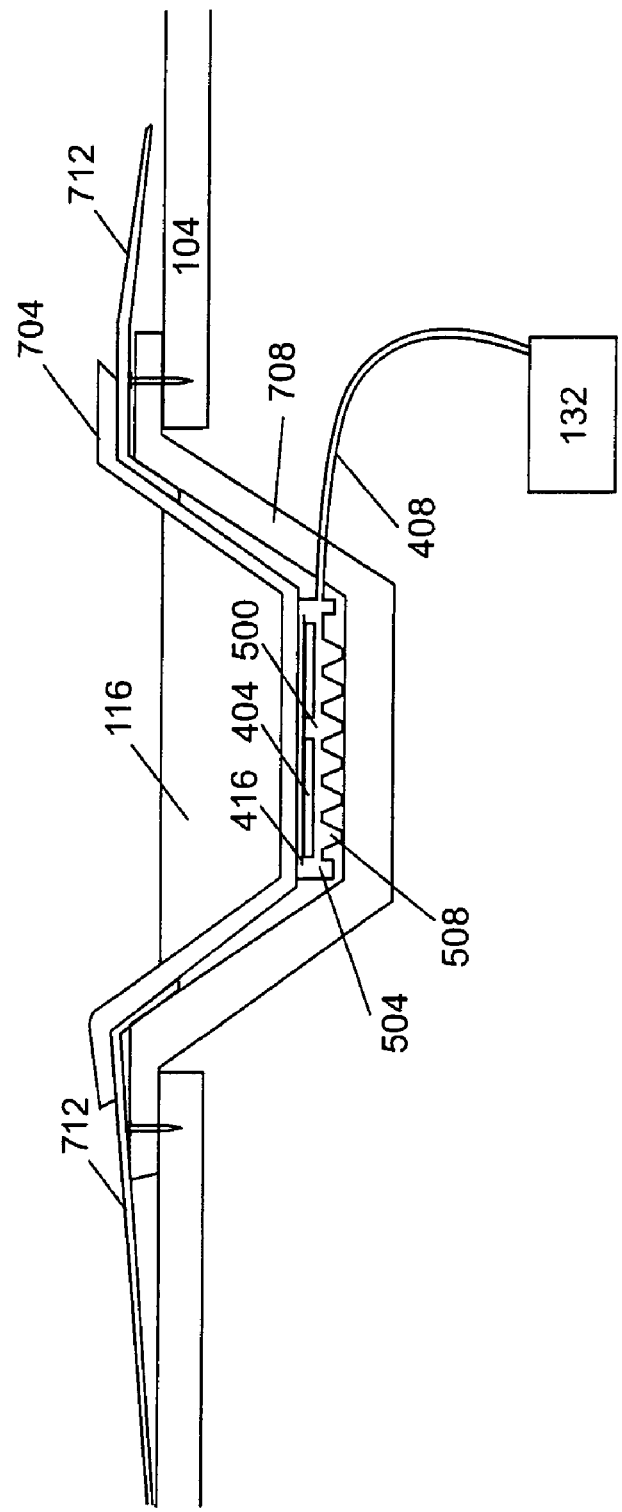
FIG. 7 provides an illustration of a cross section of the various components in a system implementing some of the teachings of the present invention.

FIG. 7 provides an illustration of a cross section of the various components in a system implementing some of the teachings from the present invention. Sterile fluid 116 is placed in removable basin 704 which mates with a surgical drape 712 with a hole for the removable basin 704. The surgical drape may be connected to the removable basin or may simply rely on the substantial overlap between the upper wall of the removable basin and the rim with the surgical drape 712 in order to maintain isolation of the sterile field from the rest of the liquid warming device. The connection between the surgical drape 712 and the removable basin 704 can done in a number of ways including using heat to tack or seal the surgical drape 712 to the removable basin 704. Alternatively, the opening in the surgical drape 712 can be sized smaller than necessary for the removable basin to fit such that the insertion of the removable basin stretches and deforms the drape hole to form a friction fit.

The removable basin 704 rests on warming pad 500. As the warming pad 500 is adapted to bend and to indent in order to increase the contact area between the warming pad 500 and the removable basin 704, the air gaps resulting from a lack of contact are eliminated or at least substantially reduced. A portion of the ability to conform to the bottom of the removable basin 704 comes from the ability of the array of protrusions 508 to bend. In a preferred embodiment the outer ring 504 is not in contact with the bottom of the integrated basin 708 as the protrusions extend below the bottom of the outer rim 504. (Note that the protrusions are drawn to be illustrative of the concept and actual protrusions are apt to be smaller and much more numerous).

The heat from heaters 404 is distributed by heat distribution layer 416 which is adapted to allow the warming pad 500 to bend to adjust to the bottom of the removable basin 704. As the heaters 404 and heat distribution layer 416 are located close to the surface of the heating pad 500, the heating pad material is not a significant impediment to the transfer of heat. In a preferred embodiment, the heat distribution layer 416 is designed to have a low thermal mass so that the heat distribution layer 416 does not add a significant delay in the heating or cooling of the top of the warming pad 500.

The wires 408 including the heat measurement indication from the heat sensor (not shown in FIG. 7) interact with controller 132 after passing through an opening in an integrated basin 708.

ALTERNATIVE EMBODIMENTS

As is often the case, a radical change in design provides new features that can be used to make less radical changes to prior art solutions. Thus the warming pad that is well suited for interacting with a removable basin has many desirable features that make it well suited for use with a surgical drape based solution.

Figure 8:
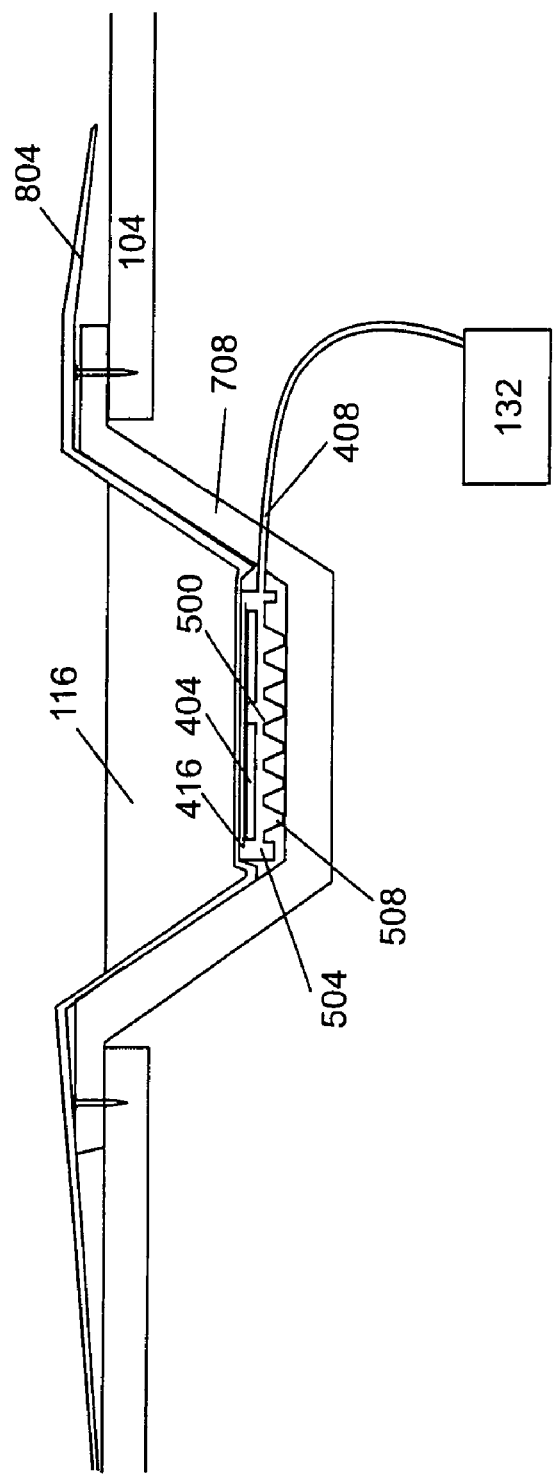
FIG. 8 illustrates an alternative embodiment with a surgical drape in direct contact with the warming pad.

In FIG. 8, sterile fluid 116 rests inside surgical drape 804. Surgical drape 804 lies on warming pad 500. While in the case of a drape, the ability of the warming pad 500 to conform to the shape of the fluid holding drape is not particularly important, other features of the warming pad do make it a better solution.

First, the placement of the heaters up high in the warming pad cross section to minimize the insulating effect of the pliable warming pad material is helpful. Second the use of the heat distribution layer 416 helps maintain a consistent temperature across the heated area of the drape. Third, the low thermal mass of the heat distribution layer 416 increases the responsiveness of the system. Placement of the heat sensor 412 in the heating pad 500 increases the accuracy of the measurement and decreases the lag time between a temperature change inside the heating pad and the receipt of that status change by the controller 132.

Fourth, the use of protrusions 508, especially protrusions that extend beyond the outer rim 504 make the warming pad 500 pliable so that the warming pad will distort to absorb energy from an implement dropped into the cavity formed in the sterile drape 804 to reduce the chance that the impact will damage the sterile drape.

Figure 9:
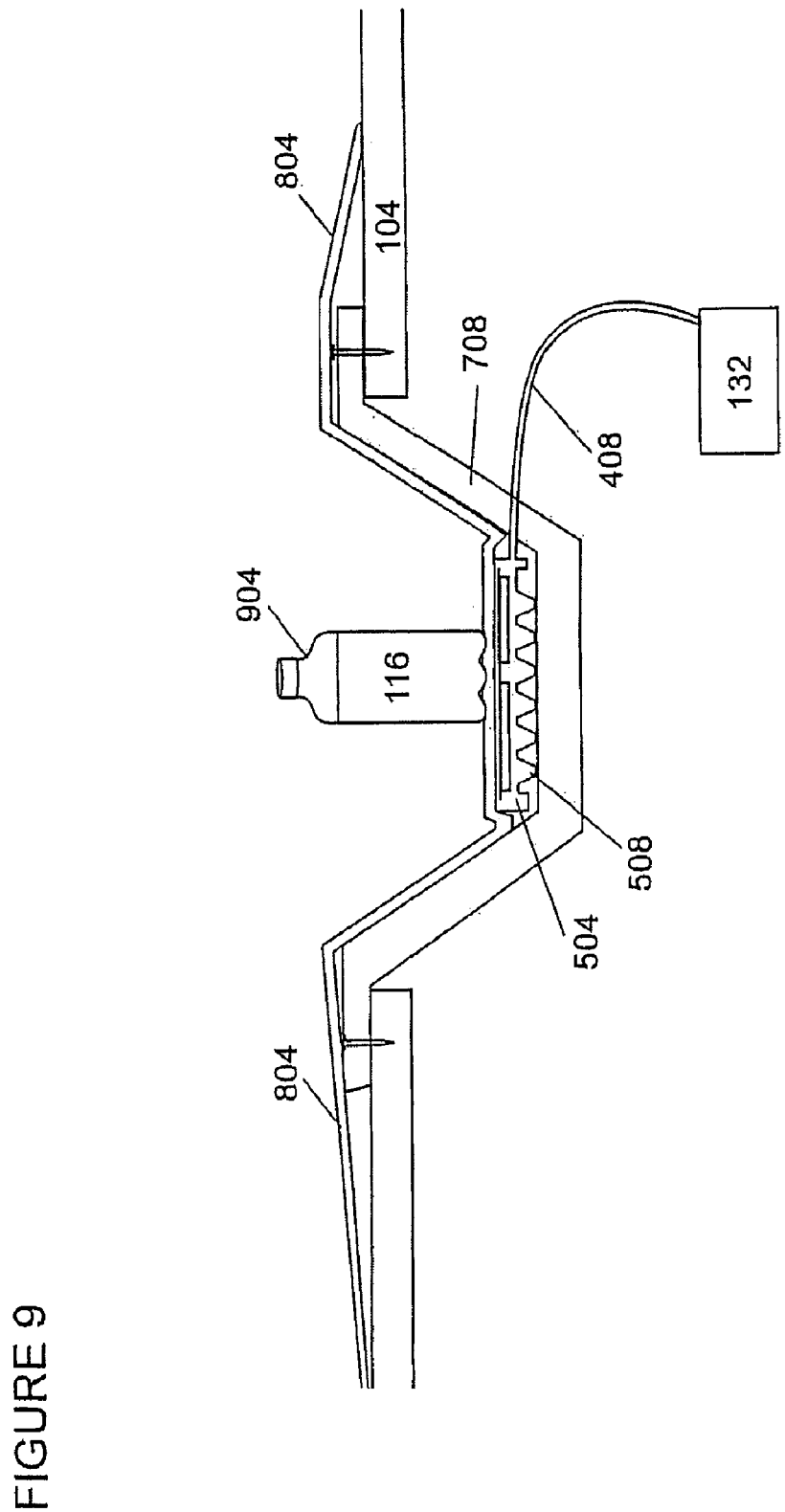
FIG. 9 illustrates an alternative embodiment with a sterile medical container above a draped pad where the pad is made in accordance with the present invention.

Another use of the present warming pad is to place a sterile medical container 904 of sterile fluid 116 directly on the draped warming pad as shown in FIG. 9. As the sterile medical container 904 is apt to have ridges in the bottom of the container to strengthen the container, the ability of the warming pad to conform to irregular shape of the sterile medical container 904 is beneficial. As a sterile medical container with sterile fluid below the target temperature will create a localized heat draw on the surface of the warming pad, the heat distribution layer 416 will convey heat from other portions of the warming pad to this area of high heat draw.

The description of preferred embodiments set forth above teaches that it is desirable for the heat distribution layer to be thin so that it has a low thermal mass and thus improves the response time of the warming pad by removing some of the lag time in moving from one temperature to another. Another advantage of having a thin heat distribution layer is that when using a solid material such a copper, a thin layer has less resistance to bending than a thick layer. In contrast, a thick layer has the advantage of promoting a more uniform distribution of heat.

To the extent that thermal mass/response time is not critical in a given application, then the tradeoff between better heat distribution and sufficient pliability may lead to the use of two or more layers of heat distribution material as this will provide multiple levels of heat distribution but the aggregated resistance to bending offered by two or more thin layers of heat distribution material can be less than the one thicker layer. Care must be taken to promote good thermal contact between layers so that gaps between layers do not act as thermal insulators.

Yet another alternative embodiment uses a non-planar warming pad. The examples of the present invention described above were all substantially planar warming pads atop a set of protrusions. It can be appreciated that a non-planar warming pad with walls sized to make contact with the walls of a removable basin would provide additional areas of contact between the warming pad and the removable basin and thus would increase the ability of the warming pad to provide heat to the sterile fluid to quickly heat the sterile fluid without using unduly high temperatures. (The use of the plural word "walls" is to be considered generic and include a one wall perimeter around a curved shape as well as the various walls of a polygon)

Figure 10:
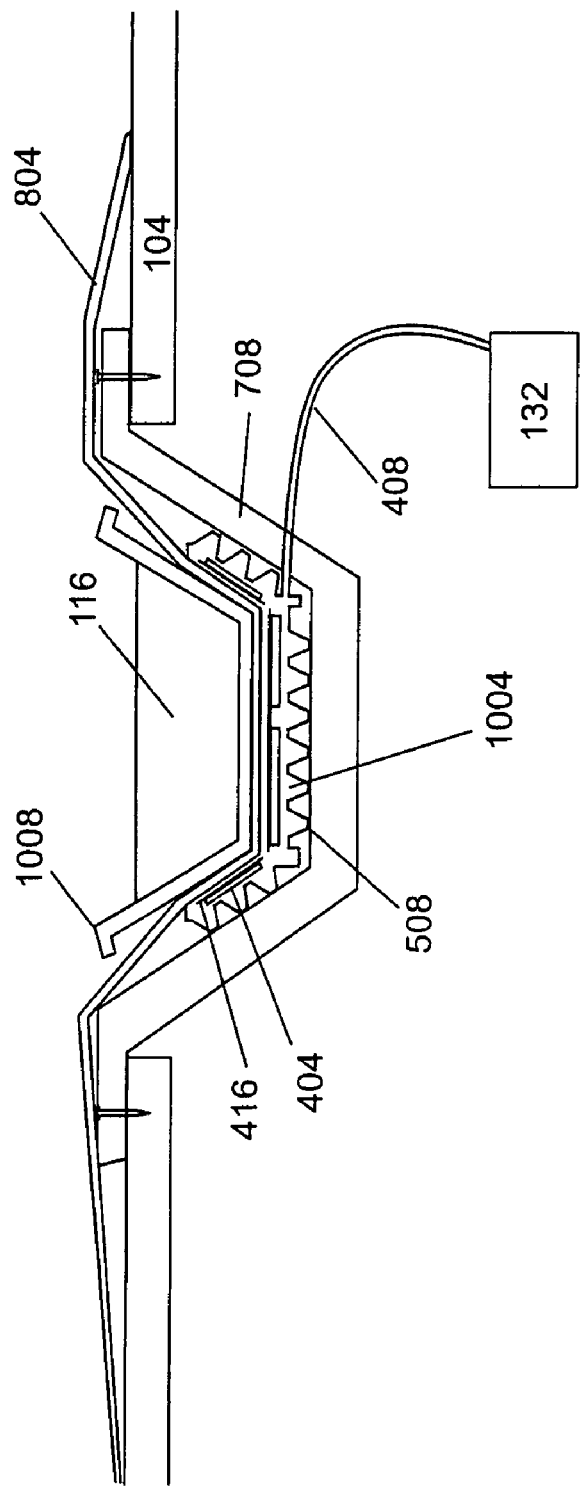
FIG. 10 illustrates the concept of a warming pad with side walls.

FIG. 10 illustrates this concept. A warming pad 1004 with side walls creates a basin shaped container within the integrated basin 708. The warming pad 1004 includes heat distribution layer 416 and optionally additional heaters 404. The additional heaters can be part of one multi-zone heater, or can be independent heaters, possibly independently monitored and controlled from the heater sections located in the planar portion of the warming pad. While it is advantageous for the heat distribution layer in the side walls to connect to the planar portion, it is not required. Surgical drape 804 covers the warming pad 1004.

As shown in FIG. 10, removable basin 1008 rests inside the draped cavity within warming pad 1004. Sterile fluid 116 is placed in the removable basin 1008.

Note that in the preferred embodiment, the height of the side walls of the warming pad 1004 are reflective of the fluid level expected in a "full" basin which is significantly less than the total height of the side walls of the removable basin. For example, the height of the side walls may be of the magnitude of two inches.

In another variation of the concept expressed in FIG. 10, the removable basin 1008 could be omitted and the sterile fluid placed directly in the cavity formed by the sterile drape 804, analogous to the concept illustrated in FIG. 8. Warming pad 1008 with heated side walls would allow for quicker heating of the sterile fluid in the drape 804, though care would need to be taken to keep an adequate fluid level so that dry drape above the water line is not exposed to heat from the side walls beyond what can be tolerated by the drape.

Figure 11:
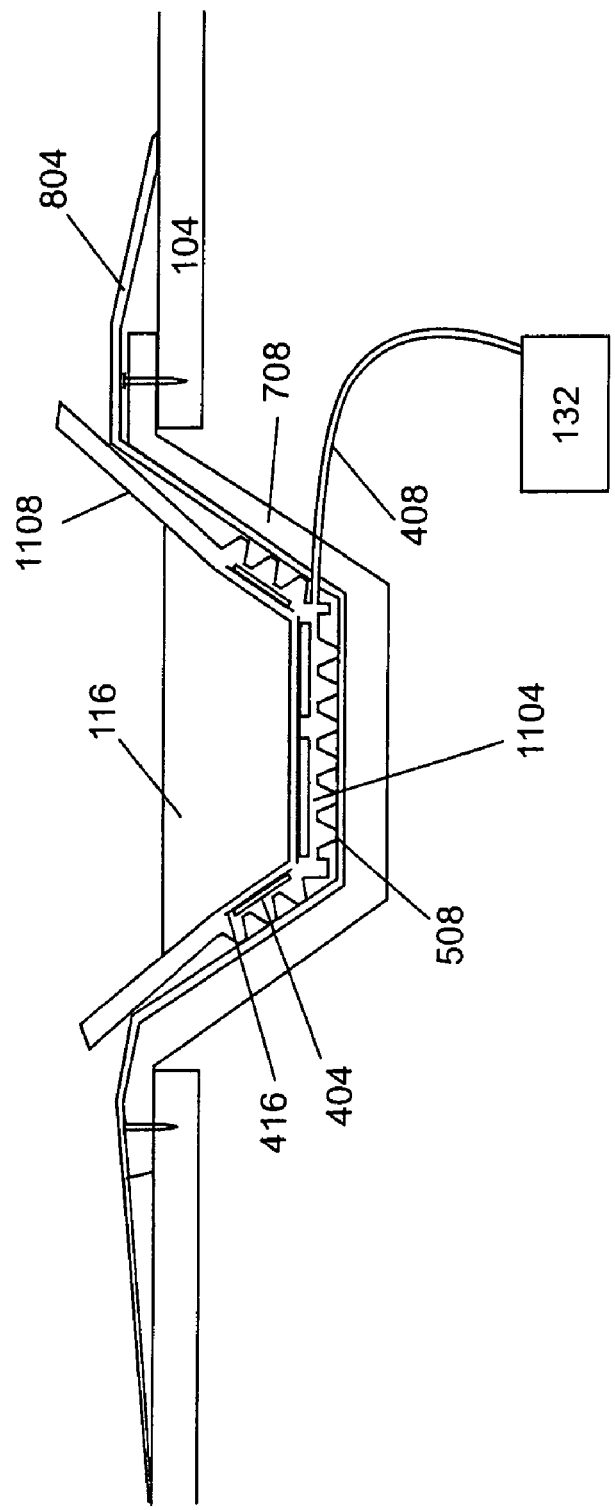
FIG. 11 illustrates a warming pad with side walls that serves as a container for the sterile fluid to be heated.

In yet another variation of the concept expressed in FIG. 10, FIG. 11 illustrates a warming pad basin 1104 having extended the side walls 1108 beyond the zone with the heater 404 and heat distribution layer 416. This warming pad basin 1104 would serve as a sterile removable basin with integral heater(s). The sterile fluid 116 could be placed directly in the sterile warming pad basin 1104. The sterile warming pad basin 1104 would rest upon a drape 804 as the drape would isolate the sterile field from the non-sterile portions of the liquid warming device cabinet. A hole (not shown) in the drape 804 allows the passage of the wires 408 from the sterile warming pad basin 1104 to connect to the rest of the warming basin cabinet. In order to protect the integrity of the sterile field, it is advantageous to place this hole in the drape below where the sterile warming pad basin 1104 will be placed. Alternatively, a drape with a larger hole that would allow the warming pad basin 1104 to pass through the hole could be used. Contingent on the process used to sterilize the sterile removable warming pad basin between uses, it may be advantageous to use single-use sterile wires to make the connection from warming pad basin 1104 to liquid warming device cabinet rather than subject wires to the sterilization process.

In the event that the warming pad basin will not be used to heat a separate removable basin, then the warming pad basin could be made without the array of protrusions 508 as there will not be a need to conform the shape of the warming pad basin to the bottom and walls of a removable basin.

In yet another permutation, a sterilized warming pad basin 1104 with elongated side walls or sterilized warming pad 500 could be placed directly in a sterile plastic basin and the sterile fluid poured over the warming pad. The sterile plastic basin would provide peace of mind that the sterile fluid would be contained in a sterile field without relying on the structural integrity of the warming pad basin 1104. The thermal transfer rate would be enhanced for either pad as the pad would be in direct contact with the sterile fluid. Optionally, planar or non-planar warming pads intended for use inside a plastic basin could be created without protrusions 508.

The wires from the warming pad basin or warming pad would advantageously connect to a separate unit containing the controller 132, power supply, controls and other equipment. The separate unit could be non-sterile and located under a surgical draper or located down below knee level as the area immediately above the floor is not part of the sterile field. If the warming pad is to be re-sterilized for subsequent use, then it may be advantageous to provide single use sterile wiring to run from the warming pad or warming pad basin to the controller.

An additional need for warming in an operating room is to apply heat to surgical slush. Surgical slush is sometimes handled in a second integrated basin in a device that provides heated surgical fluids, sometimes surgical slush is handled in a liquid warming device that can alternatively provide heated surgical fluid or surgical slush, and sometimes the surgical slush is handled in a device dedicated to handling of surgical slush. These devices have a warming function to selectively change the slush to liquid, especially at the edges of the collection of slush closest to the basin walls in order to facilitate obtaining slush from the basin. Systems with a slush warming cycle also have a need for efficient application of heat without hot spots. While the teachings of the present invention have been illustrated in the context of heating sterile fluid, these teachings can be extended for use in providing heat to selectively melt sterile slush. Any claims that follow should be read to be inclusive of slush warming operations unless the claim is explicit in excluding slush warming operations.

One of skill in the art will recognize that alternative embodiments set forth above are not universally mutually exclusive and that in some cases alternative embodiments can be created that implement two or more of the variations described above. In a like manner, one of skill in the art will recognize that certain aspects of the present invention can be implemented without implementing all of the teachings illustrated in the various disclosed embodiment. Such partial implementations of the teachings of the present invention fall within the claimed subject matter unless the claims are explicit in calling for the presence of additional elements from other teachings.

Those skilled in the art will recognize that the methods and apparatus of the present invention have many applications and that the present invention is not limited to the specific examples given to promote understanding of the present invention. Moreover, the scope of the present invention covers the range of variations, modifications, and substitutes for the system components described herein, as would be known to those of skill in the art.

The invention claimed is:

1. A method of heating fluid in a removable basin, the basin comprising an inside and an outside and a rim extending out essentially horizontally from the top of the inside of the basin, with the inside adapted to contain water, the outside having a bottom, the method comprising:
    placing the bottom of the basin on a pliable pad in a liquid warming device, the basin encircled by a drape such that the bottom of the basin contacts the pad and not the drape and the drape extends outward from the basin beyond the rim of the basin to cover at least a portion of the liquid warming device;
    adding fluid to the basin; and
    applying heat from a heater in the pad through the top of the pad which has substantially conformed to the shape of the bottom of the basin.

2. The method of claim 1 wherein further comprising the step of deforming a set of protrusions extending from a bottom of the pad to deform the pad to assist the top of the pad in substantially conforming to the shape of the bottom of the basin.

3. The method of claim 1 wherein the step of placing the bottom of the basin encircled by the drape on the pad in the liquid warming device further comprises the step of positioning a drape with a hole in the drape to place the hole over a cavity in the liquid warming device, the cavity containing the pad such that the basin is placed on the pad by placing the bottom of the basin through the hole in the drape.

4. The method of claim 1 wherein the step of placing the bottom of the basin encircled by the drape on the pad in the liquid warming device further comprises the step of bonding the drape to the exterior of the basin below the top face of the rim and above the bottom of the basin such that the bottom of the basin with the bonded drape is placed in a cavity in the liquid warming device containing the pad.

5. A liquid warming device comprising:
a sterile drape in a cavity of the liquid warming device, a portion of the drape extending out beyond the cavity to cover at least a portion of the liquid warming device to separate the covered portion of the liquid warming device from a sterile field; another portion of the drape resting on a pad, the pad comprising:
a first layer of pliable thermally insulative material above a set of at least one heating unit which is above a second layer of pliable thermally insulative material, at least twice as thick as the first layer such that more heat leaves the pad through top of the first layer than through the bottom of the second layer;
such that the drape is partially protected from mechanical damage from a dropped item dropped into the draped cavity as the pad will deform upon impact from a dropped item onto the draped pad.

6. The liquid warming device of 5 wherein the pad further comprises a set of protrusions extending downward from the second layer of pliable thermally insulative material such that a portion of the deformation of the pad upon impact from a dropped item comes from deformation of at least one of the set of protrusions.

7. A liquid warming device comprising:
a sterile drape in a cavity of the liquid warming device, a portion of the drape extending out beyond the cavity to cover at least a portion of the liquid warming device to separate the covered portion of the liquid warming device from a sterile field; another portion of the drape resting on a pad, the pad comprising:
a layer of pliable thermally insulative material above a set of at least one heating unit;
such that the drape is partially protected from mechanical damage from a dropped item dropped into the draped cavity as the pad will deform upon impact from a dropped item onto the draped pad.

* * * * *